United States Patent
Hickey et al.

(10) Patent No.: US 10,926,022 B2
(45) Date of Patent: Feb. 23, 2021

(54) TIP DETECTION APPARATUS AND METHOD FOR MEDICAL DEVICE

(71) Applicant: Johnson & Johnson Surgical Vision, Inc., Santa Ana, CA (US)

(72) Inventors: Lauren M. Hickey, Torrance, CA (US); Kyle E. Lynn, Los Angeles, CA (US); Johan W. Steenstra Toussaint, Redondo Beach, CA (US); Frederick C. Lee, Tustin, CA (US); James W. Staggs, Laguna Niguel, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 670 days.

(21) Appl. No.: 15/427,790

(22) Filed: Feb. 8, 2017

(65) Prior Publication Data

US 2017/0224888 A1    Aug. 10, 2017

Related U.S. Application Data

(60) Provisional application No. 62/293,283, filed on Feb. 9, 2016.

(51) Int. Cl.
*A61M 3/02* (2006.01)
*A61F 9/007* (2006.01)
*A61M 1/00* (2006.01)

(52) U.S. Cl.
CPC ....... *A61M 3/0279* (2013.01); *A61F 9/00736* (2013.01); *A61F 9/00745* (2013.01);
(Continued)

(58) Field of Classification Search
CPC .............. A61M 1/0064; A61M 1/0084; A61M 2205/14; A61M 2205/3334;
(Continued)

(56) References Cited

U.S. PATENT DOCUMENTS

2003/0060863 A1* 3/2003 Dobak, III ................. A61F 7/12
607/104
2010/0280439 A1* 11/2010 Kuebler .............. A61M 1/0031
604/35
(Continued)

FOREIGN PATENT DOCUMENTS

EP    2379126 B1    4/2015

OTHER PUBLICATIONS

International Preliminary Report on Patentability for Application No. PCT/US2017/017006, dated Aug. 23, 2018, 9 pages.

*Primary Examiner* — Nathan R Price
*Assistant Examiner* — Melissa A Snyder
(74) *Attorney, Agent, or Firm* — Johnson & Johnson Surgical Vision, Inc.

(57) ABSTRACT

An apparatus and method of detecting an interchangeable tip of a handpiece of an ocular surgical system is disclosed. The interchangeable tip of the system includes an irrigation port that receives fluid flowing from an irrigation source and an aspiration port that removes or aspirates fluid and/or materials from the surgical field, in particular a patient's eye, through use of an aspiration source or pump. The method comprises attaching the interchangeable tip to the handpiece, introducing fluid flow into the system and determining the fluid flow rate of fluid flow in the system, determining the pressure of fluid flowing into the interchangeable tip, determining the pressure of fluid flowing out of the interchangeable tip and comparing the flow rate and pressure information to known flow rate and pressure readings of known types of interchangeable tips to determine the type of interchangeable tip being used.

24 Claims, 7 Drawing Sheets

(52) U.S. Cl.
CPC ........ *A61M 1/0025* (2014.02); *A61M 1/0058* (2013.01); *A61M 1/0064* (2013.01); *A61M 1/0076* (2013.01); *A61M 1/0084* (2013.01); *A61M 3/022* (2014.02); *A61M 3/0208* (2014.02); *A61M 3/0212* (2014.02); *A61M 3/0216* (2014.02); *A61M 3/0233* (2013.01); *A61M 1/0031* (2013.01); *A61M 2205/14* (2013.01); *A61M 2205/3331* (2013.01); *A61M 2205/3334* (2013.01); *A61M 2205/50* (2013.01); *A61M 2205/502* (2013.01); *A61M 2205/6018* (2013.01); *A61M 2210/0612* (2013.01)

(58) Field of Classification Search
CPC ............. A61M 2206/10; A61M 3/0279; A61F 9/00745; A61F 9/00736
See application file for complete search history.

(56) References Cited

U.S. PATENT DOCUMENTS

| | | | |
|---|---|---|---|
| 2012/0072197 A1 | 3/2012 | Ovchinnikov | |
| 2014/0114237 A1 | 4/2014 | Gordon | |
| 2014/0276897 A1* | 9/2014 | Rockley | A61F 9/00736 606/107 |

* cited by examiner

TIP DETECTION APPARATUS AND METHOD FOR MEDICAL DEVICE

CROSS-REFERENCE

This application claims the benefit under 35 U.S.C. § 119(e) of U.S. Provisional Application No. 62/293,283, filed Feb. 9, 2016, the full disclosures of which are incorporated herein by reference.

BACKGROUND

Field of Invention

The present disclosure relates generally to medical apparatuses and methods that provide pressurized infusion of liquids for ophthalmic surgery, and more particularly, is directed to an intraocular lens removal device with an irrigation source and an aspiration pump.

Description of Related Art

Ophthalmic surgical apparatuses typically include operating controls for regulating settings or functions of the apparatus. Numerous types of apparatuses include as part of the apparatus, a hand-held medical implement or tool, such as a handpiece with a tip. Operation of the tool requires control of various operating settings or functions based on the type of tool used. Such apparatuses typically include a control module, power supply, an irrigation source, one or more aspiration pumps, as well as associated electronic hardware for operating a multifunction handheld surgical tool in order to sonically emulsify eye tissue, irrigate the eye with a saline solution, and aspirate the emulsified lens from the eye.

A number of medically recognized techniques are utilized for crystalline lines removal based on a variety of technologies, for example, phacoemulsification or vitrectomy. Phacoemulsification includes making a corneal and/or scleral incision and the insertion of a phacoemulsification handpiece that includes a needle or tip that is ultrasonically driven to emulsify, or liquefy, the lens. A phacoemulsification system typically includes a handpiece coupled to an irrigation source and an aspiration pump. The handpiece includes a distal tip that emits ultrasonic energy to emulsify a crystalline lens within the patient's eye. The handpiece includes an irrigation port proximal to the distal tip and coupled to the irrigation source via an irrigation input line. The handpiece further includes an aspiration port at the distal tip that is coupled to the aspiration pump via an aspiration output line. Concomitantly with the emulsification, fluid from the irrigation source (which may be a bottle or bag of saline solution that is elevated above the field of surgery) is irrigated into the eye via the irrigation line and the irrigation port. This fluid is directed to the crystalline lens in the patient's eye in order to break apart the lens into small pieces and carry the crystalline lens material away. The irrigation fluid in the patient's eye and the crystalline lens material is then aspirated or removed from the eye by the aspiration pump and line via the aspiration port. In some instances, the aspiration pump may be in the form of, for example, a peristaltic or positive displacement pump. Other forms of aspiration pumps are well known in the art, such as vacuum pumps. Other medical techniques for removing crystalline lenses also typically include irrigating the eye and aspirating lens parts and other liquids. Additionally, some procedures may include irrigating the eye and aspirating the irrigation fluid without concomitant destruction, alteration or removal of the lens.

Phacoemulsification and vitrectomy procedures may require fluid control, namely control over aspiration and irrigation to the ocular region, and employ a handpiece that is typically controlled electrically in order to, for example, control the flow of fluid through the handpiece and tip. Various types, sizes and shapes of tips are known depending on the desired surgical outcomes, and may be interchangeably connected to the handpiece before, during or after surgery. For instance, some tips may include larger irrigation ports to permit more fluid flow into the eye during surgery, while others may vary the location or shape of the irrigation port to direct the flow in specific locations in the eye. Similarly, the aspiration port may be sized according to the aspiration needs of the crystalline lens material, or be provided in a specific location or shape on the tip to ensure optimal removal of the irrigation fluid and crystalline lens material.

As it is well known, for these types of surgical procedures, it is necessary to understand and account for specific characteristics or surgical settings before, during or after the procedure. For instance, it may be necessary to maintain a stable volume of liquid in the anterior chamber of the eye, and this is accomplished by irrigating fluid into the eye at the same rate as aspirating fluid and lens material from the eye. Accordingly, the characteristics of a selected tip of the handpiece, for instance the size and character of the irrigation port and the aspiration port, must be accounted for when determining other surgical settings or controls of the system. For instance, other control can be provided by various device components and operations for the phacoemulsification, diathermy or vitrectomy machine, including control of fluid flow, entry into various modes, electrical parameters, speed parameters (e.g. ultrasonic or cut speed), and so forth. When a specific tip is attached to the handpiece, the characteristics of the specific tip must be accounted for in the system to adjust other controls or settings.

In prior systems, the control and settings of the system may be electronically controlled or modified by use of a computer system. If characteristics of the tip are predetermined and uniform, the computer system would permit a surgeon or user to select a specific tip for use with the handpiece from a display, and thereafter the computer could automatically adjust the controls or settings based on the dimensions or characterizations of the selected tip. Alternatively, surgeons or users may be provided with default settings for a specific tip size, and may thereafter enter those settings into the computer system when a specific tip is selected. Either way, the surgeon or user must interface with the display system during use of the device, which can cause undesirable delay in the procedure, potential of contamination or distraction to the surgeon or user, or the introduction of human error to the process of selecting appropriate control and settings based on the specific tip being used.

Based on the foregoing, it would be advantageous to provide a means for providing automatic detection of a specific tip by the computer and calibration or adjustment of the system settings by the computer without user intervention. Such a design would afford a surgeon the ability to perform desired phacoemulsification, diathermy, or vitrectomy functions with less need to worry about modifying or adjusting the settings of the system based on the tip selected. This is particularly true when a single surgical operation would require use of more than one tip type. Moreover, such a design would reduce the introduction of human error, distraction, or contamination into the surgical process, as the user or surgeon would not need to interact with the display or insert information into the display in order for the system's settings to be calibrated based on the specific tip selected.

SUMMARY

According to one aspect of the present invention, an ocular surgical apparatus comprises an intraocular lens removal device having a handpiece with interchangeable tips, the device further comprising a subsystem or electronic system of the apparatus that detects the pressure of the fluid flowing through the system before and after the fluid flows the tip of the handpiece, and thereafter determines the size and other characteristics of the interchangeable tip attached to the handpiece automatically from the pressure information and adjusts any system settings or performance criteria accordingly.

Accordingly to another aspect of the present invention, a method of detecting an interchangeable tip of a handpiece of a phacoemulsification/diathermy/vitrectomy system comprises attaching the interchangeable tip to the handpiece, introducing fluid flow into the system, creating a vacuum in the fluidic system, determining the pressure of fluid flowing into the interchangeable tip, determining the pressure of fluid flowing out of the interchangeable tip, determining the size or characteristic of the interchangeable tip based on the difference in pressure, determining desired surgical settings or system performance metrics based on the interchangeable tip detected, and applying those surgical settings or metrics to the system automatically in order to have desired system performance during the surgical operation.

Other systems, methods, features and advantages of the invention will be or will become apparent to one of skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The organization and manner of the structure and function of the disclosure, together with the further objects and advantages thereof, may be understood by reference to the following description taken in connection with the accompanying drawings, and in which.

DETAILED DESCRIPTION

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

A system and method for detecting interchangeable tips of a handpiece of a surgical system utilizing vacuum-based aspiration sub-system, which can be applied to any system, medical or non-medical, are disclosed herein. In illustrative embodiments, the system and method include means for automatically detecting the type of interchangeable tip connected to the handpiece and automatically calibrating or adjusting performance or settings of the system based on the characteristics of the tip attached to the handpiece Embodiments of a subsystem and method will be discussed herein with a particular emphasis on a medical or hospital environment where a surgeon or health care practitioner performs. For example, an embodiment is a phacoemulsification surgical system that comprises an integrated high-speed control module for a vitrectomy handpiece that can accept a variety of interchangeable tips. The system further comprises sensors to detect the pressure of fluid flowing through the system, and in particular the pressure of fluid before and after the fluid flows through an interchangeable tip attached to the handpiece, and a processor that determines the size or type of the interchangeable tip based on known or predetermined pressure differentials known for various tips. The system further comprises a processor that can control, adjust or set various characteristics of the system to control a high-speed pneumatic vitrectomy handpiece.

Figure 1:
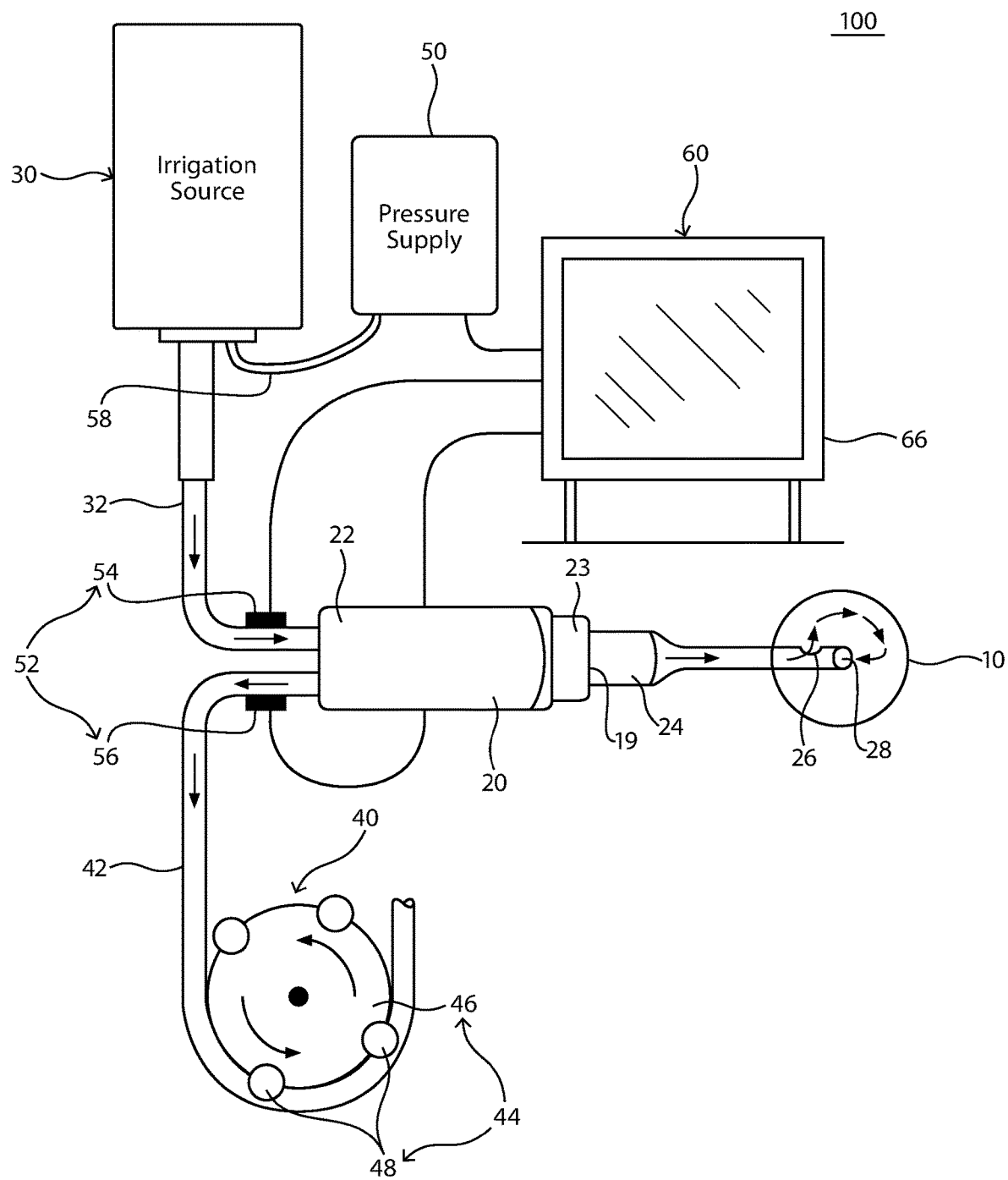
FIG. 1 illustrates a diagram of an exemplary phacoemulsification/diathermy/vitrectomy system in accordance with the present disclosures, the system including a handpiece for use during a surgical procedure.

FIG. 1 illustrates an exemplary phacoemulsification/diathermy/vitrectomy system 100. As illustrated, the system 100 includes, for example, a handpiece or wand 20, an irrigation source 30, an aspiration source 40, an optional pressure supply 50, and a control module 60. In this embodiment, fluid is controllably directed through the system 100 in order to irrigate a patient's eye, illustrated representatively at 10, during an ocular surgical procedure. Various embodiments of the handpiece 20, irrigation source 30, aspiration source 40, pressure supply 50 and control module 60 are well known in the art and are embodied in this disclosure. For example, irrigation source 30 may be a bag or bottle; aspiration source 40 may be a peristaltic pump, Venturi pump, a combination of said pumps, and/or similar type pumps know in the art; and pressure supply 50 may be any source known in the art to supply pressure to irrigation source 30, e.g. various types of pumps, such as, but not limited to peristaltic, Venturi, pneumatic, or a combination thereof.

As illustrated in FIG. 1, the irrigation source 30 is configured to supply a predetermined amount of fluid to the handpiece 20 for use during surgical operation. Specifically, fluid may flow from the irrigation source 30 to the handpiece 20 via an irrigation line 32. The irrigation source 30 may be any type of irrigation source 30 that can create and control a constant fluid flow such that vacuum pressure may be determined in the fluid flow, as known in the art. In illustrative embodiments, the irrigation source 30 may be configured to be an elevated drip bag 34 that supplies a steady state of fluid to the irrigation line 32. The pressure supply 50 may be coupled to the irrigation source 30 in order to maintain a constant pressure in the irrigation source 30 as fluid exits the irrigation source 30, as is known in the industry. Other embodiments of a uniform irrigation source are well known in the art.

During the surgical procedure, it may be necessary to remove or aspirate fluid and other material from the eye. Accordingly, fluid may be aspirated from the eye via the handpiece 20 to flow through an aspiration line 42 to the aspiration source 40. The aspiration source 40 may be any type of aspiration source 40 that creates a constant fluid flow such that vacuum pressure may be determined in the fluid flow. In illustrative embodiments, the aspiration source 40 may be configured to be a flow-based pump 44 (such as a peristaltic or scroll pump) that are well known in the art. The aspiration source 40 may create an aspiration system to pump a uniform or predetermined amount of fluid and/or material out of the eye via the aspiration line 42. Other embodiments of a uniform aspiration source are well known in the art.

The handpiece 20 includes a first end 22 and a second end 23 that includes means for attaching an interchangeable tip 24. The tip 24 includes an irrigation port 26 and an aspiration port 28. The irrigation port 26 is fluidly coupled to the irrigation line 32 to receive fluid flow from the irrigation source 30, and the aspiration port 28 is fluidly coupled to the aspiration line 42 to receive fluid and/or material flow from the eye. The handpiece 20 and the tip 24 may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well known in the art. Concomitantly with the emulsification, fluid from the irrigation source 30 is irrigated into the eye via the irrigation line 32 and the irrigation port 26. During and after such emulsification, the irrigation fluid and emulsified crystalline lens material are aspirated form the eye by the aspiration source 40 via the aspiration port 28 and the aspiration line 42. Other medical techniques for removing crystalline lenses also typically include irrigating the eye and aspirating lens parts and other liquids. Additionally, other procedures may include irrigating the eye and aspirating the irrigating fluid within concomitant destruction, alternation or removal of the lens.

As illustrated in FIGS. 2 and 3A-3E, the interchangeable tip 24 may be a predetermined or uniform shape and size, and may further include various features that are beneficial to performing the surgical operation. Such tips 24 are generally known to be of uniform sizes or types in the industry, such that certain tips 24 may be considered advantageous for certain surgical maneuvers or operations. Tips of uniform size or type may be identified by specific name or product number to be an industry standard design. Surgeons or other users of such tips may have industry knowledge of the types of tips available and their varying characteristics, and may rely on the uniformity of tip types from operation to operation.

As illustrated in FIGS. 3A-3E, many different sizes and shapes of tips 24 may be known in the industry. As known in the art, the tip 24 size, and in particular the size of the irrigation port 26 and the aspiration port 28, affects the pressure or vacuum reading of the fluid flowing there through. For instance, a smaller sized irrigation port will create a higher vacuum pressure reading and vice versa. Uniform industry tip sizes may be specifically designed to create varying pressures or fluid flow into and out of the eye.

Figure 3A:
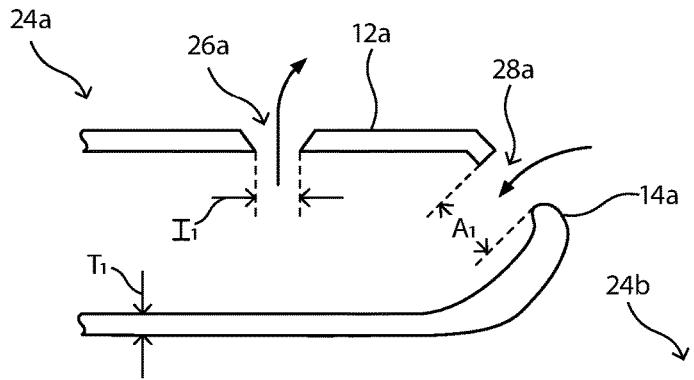
FIGS. 3A-3E are cross-sectional views of a distal end of interchangeable multipurpose phacoemulsification tips similar to those shown in FIG. 2, showing a variety of constructions for the irrigation port and aspiration ports.

As shown in FIG. 3A, a first tip 24a may include an irrigation port 26a with a predetermined shape and width $I_1$ that is positioned along the top 12a of the tip 24a and an aspiration port 28a with a different predetermined shape and width $A_1$ positioned at the end 14a of the tip 24a. The thickness $T_1$ of the first tip 24a may be equal to or smaller than the widths $I_1$ and $A_1$ of the ports 26a and 28a. The width $I_1$ of the irrigation port 26a may be smaller than the width $A_1$ of the aspiration port 28a to minimize and control the fluid flow into the eye while still permitting an appropriate amount of fluid flow and other material flow out of the eye.

Figure 3B:
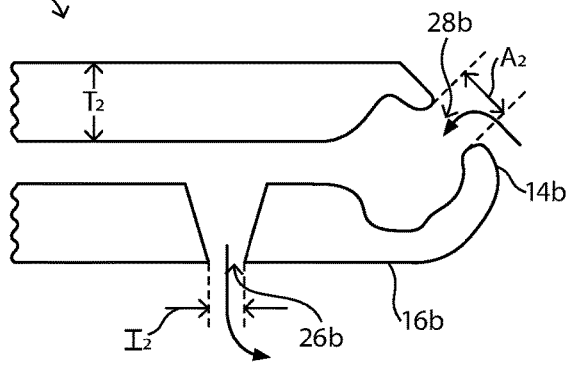
Figure 3C:
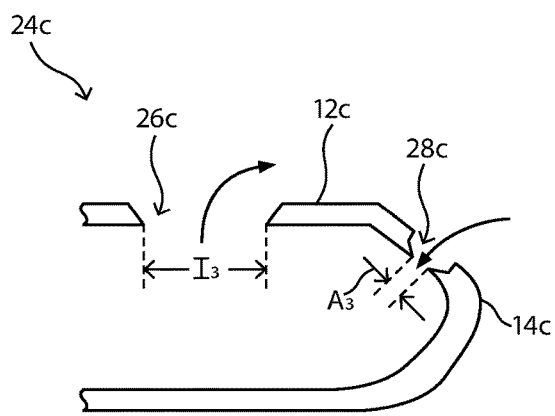

As shown in FIG. 3B, a second tip 24b may include an irrigation port 26b with a predetermined shape and width $I_2$ that is positioned along the bottom 16b of the tip 24b and an aspiration port 28b with a different predetermined shape and width $A_2$ positioned at the end 14b of the tip 24b. The thickness $T_2$ of the second tip 24b may change in diameter along the length of the second tip 24b. The location of the irrigation port 26b on the bottom 16b of the tip 24b may permit specialized fluid flow direction for unusual or difficult procedures. As shown in FIG. 3C, a third tip 24c may include an irrigation port 26c with a predetermined shape and width $I_3$ that is positioned along the top 12c of the tip 24c and an aspiration port 28c with a different predetermined shape and width $A_3$ positioned at the end 14c of the tip 24c. The width $I_3$ of the irrigation port 26c may be larger than the width $A_3$ of the aspiration port 28c to direct more fluid flowing into the eye than fluid flowing out of the eye during a procedure where more irrigation of the eye is desired.

Figure 2:
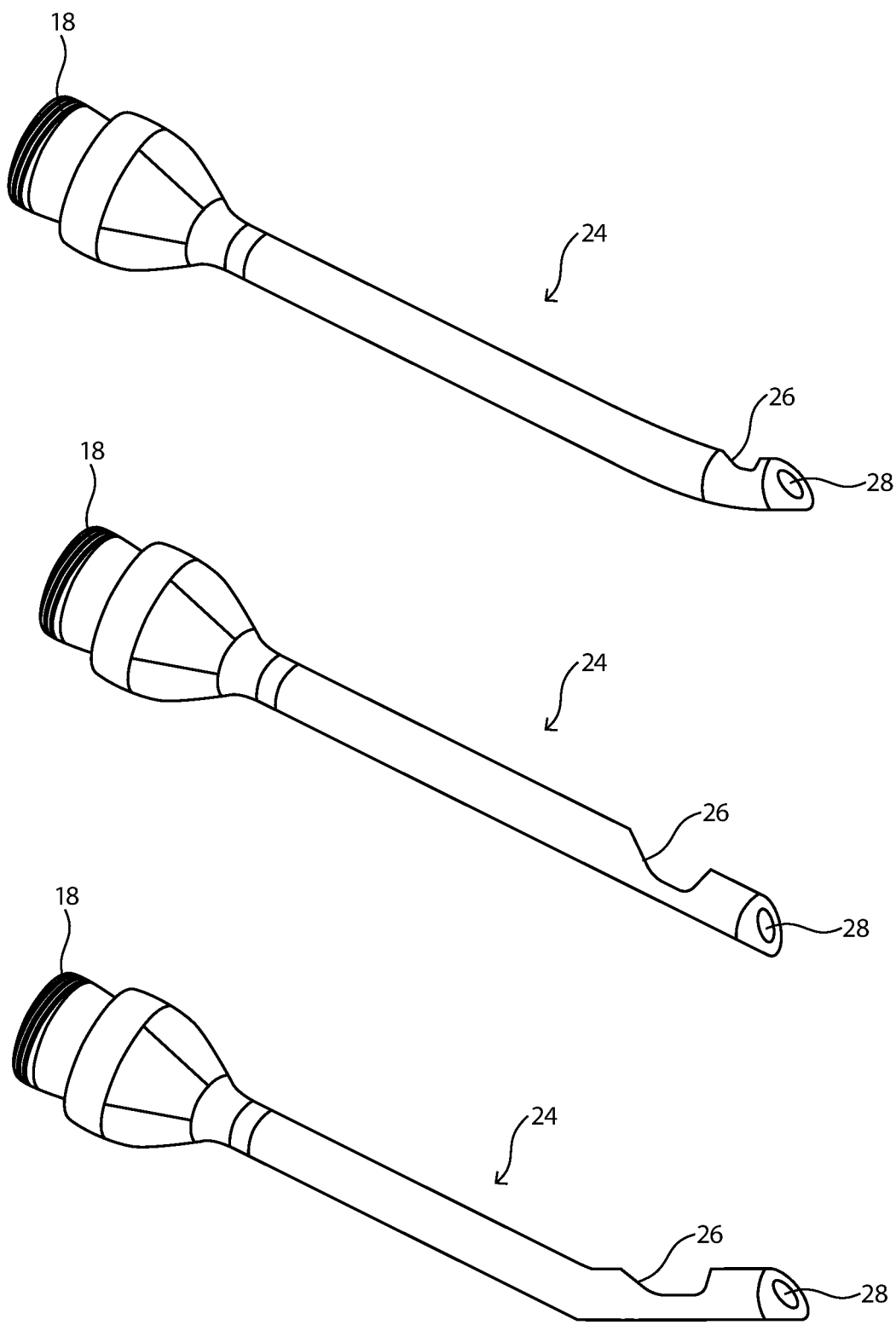
FIG. 2 is a perspective view of interchangeable multipurpose phacoemulsification tips that may be used with the handpiece of FIG. 1, with the tips being capable of connection to a distal end the handpiece and having an irrigation port and an aspiration port.
Figure 3D:
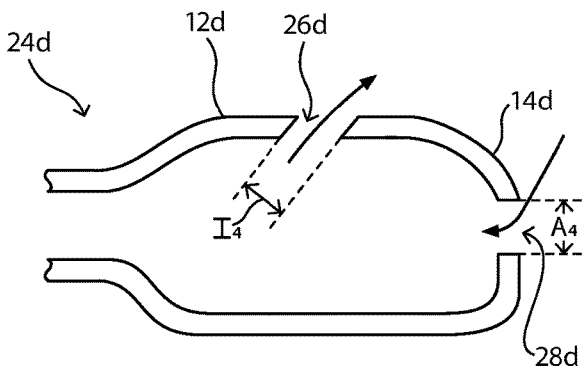
Figure 3E:
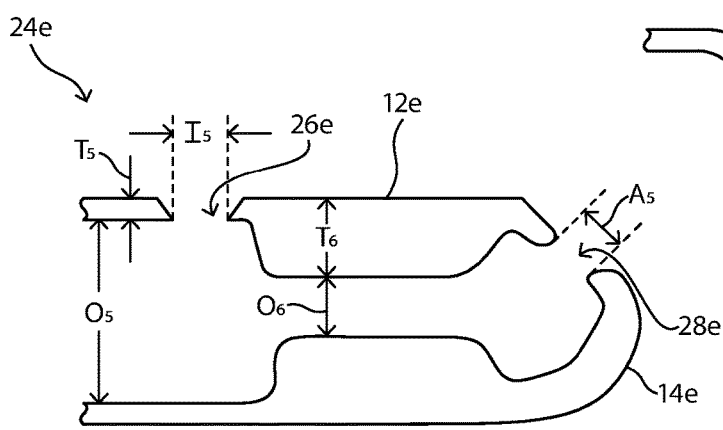

As shown in FIG. 3D, a fourth tip 24d may include an irrigation port 26d shaped to cause a predetermined angle of flow into the eye through a width $I_4$ that is positioned along the top 12d of the tip 24d and an aspiration port 28d causing a different predetermined angle of flow out of the eye through a width $A_4$ positioned at the end 14d of the tip 24d. As shown in FIG. 3E, a fifth tip 24e may include an irrigation port 26e with a predetermined shape and width $I_5$ that is positioned along the top 12e of the tip 24e and an aspiration port 28e with a predetermined shape and width $A_5$ positioned at the end 14e of the tip 24e. The irrigation port 26e may be positioned to be in fluid contact with a larger-diameter portion $O_5$ of the tip 24e to enhance fluid flow into the eye, while the aspiration port 28e may be positioned to be in fluid contact to a smaller-diameter portion $O_6$ of the tip 24e to control and direct the flow of fluid and other materials coming out of the eye. As illustrated in FIG. 2, the tips 24 may further include various shapes and lengths to accommodate needs of various surgical procedures. In other embodiments, there may be a single irrigation and aspiration port 26/28 that functions to both irrigate and aspirate the eye. Similarly, other combination may be employed. For example, a tip may include more than one single irrigation and aspiration port 26/28 that functions to both irrigate and aspirate. In other embodiments, a tip may include more than one irrigation port and/or more than one aspiration port. Such combinations may enhance the performance of the tip and may more easily accommodate features provided by the surgical console. Other embodiments of uniform or known tips are well known in the art.

In illustrative embodiments, various types of tips may be used to perform various surgical procedures throughout a single surgical operation. The tips 24 may be coupled to the handpiece 20 through any known means, including coupling a threaded portion 18 of the tip 24, as illustrated in FIG. 2, to a threaded portion 19 of the handpiece 20. During a surgical procedure, the surgeon may utilize multiple types of uniform tips throughout the procedure by attaching and removing the interchangeable tips 24. However, such a process creates inefficiencies and slows the procedure, especially because the surgeon or user must input new criteria or settings into the system to optimize operation of the system with the newly attached tip 24. As is known in the art, time is of the essence during such a surgical procedure. Therefore, there is a balance between utilizing the most comprehensive tip-selection process for optimal surgical results, which may take addition surgeon or user time to prepare for, and minimizing the duration of time during the procedure.

Figure 4:
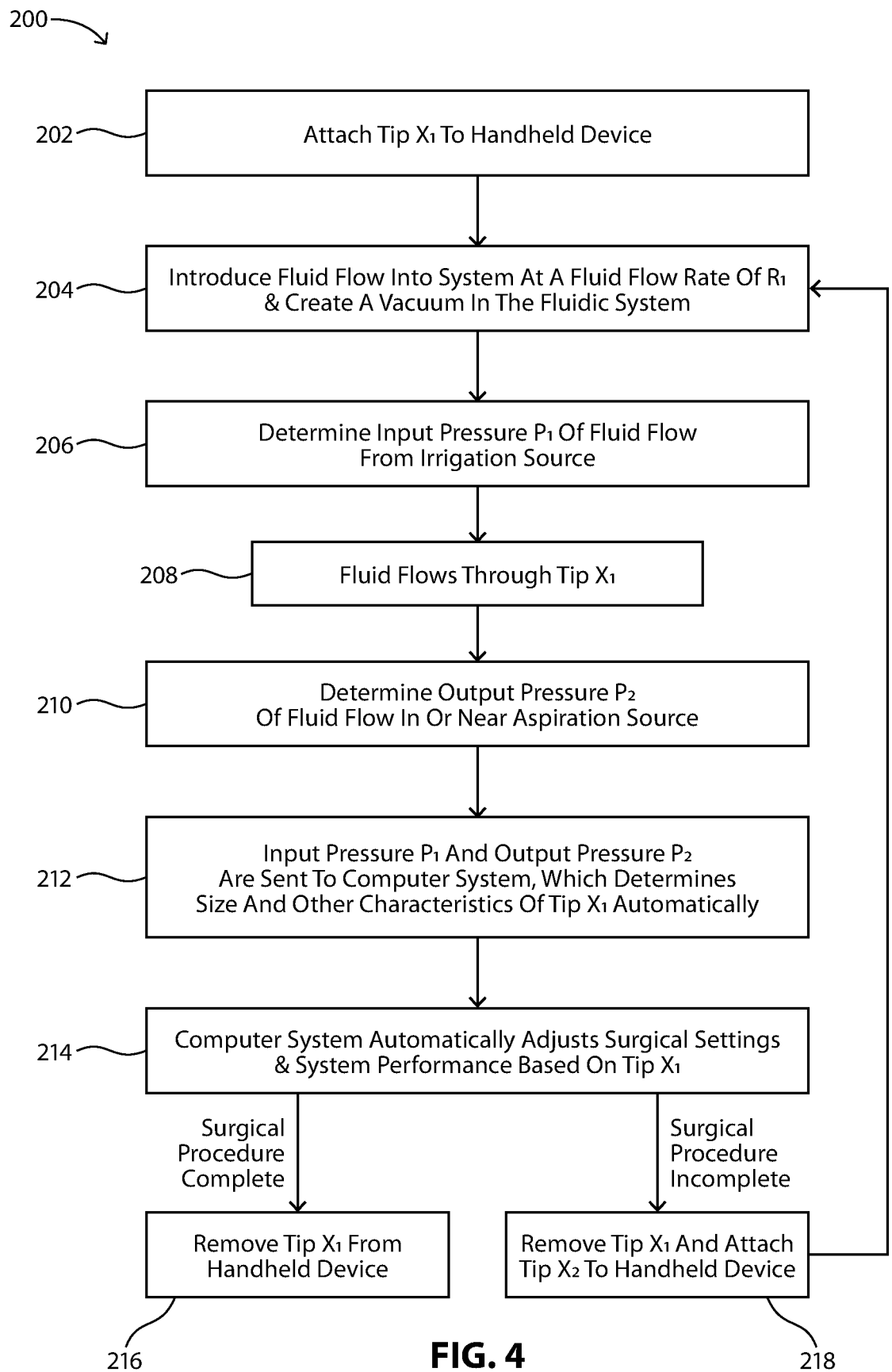
FIG. 4 illustrates a block diagram showing a flow chart of one embodiment of the method of the utilizing the system of FIG. 1 in accordance with the present disclosure to perform a surgical procedure.
Figure 5:
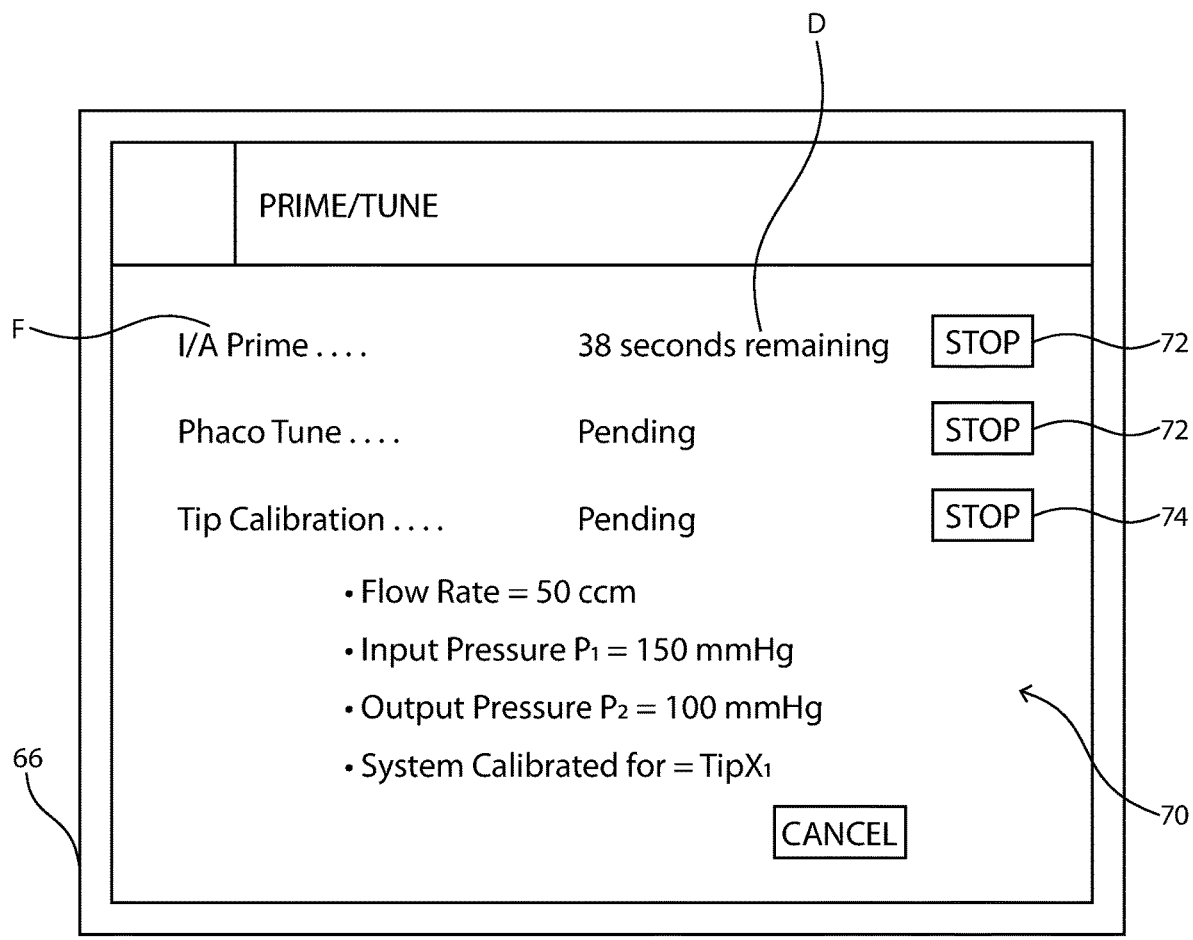
FIG. 5 illustrates an embodiment of a graphical user interface of the system of FIG. 1.
Figure 6:
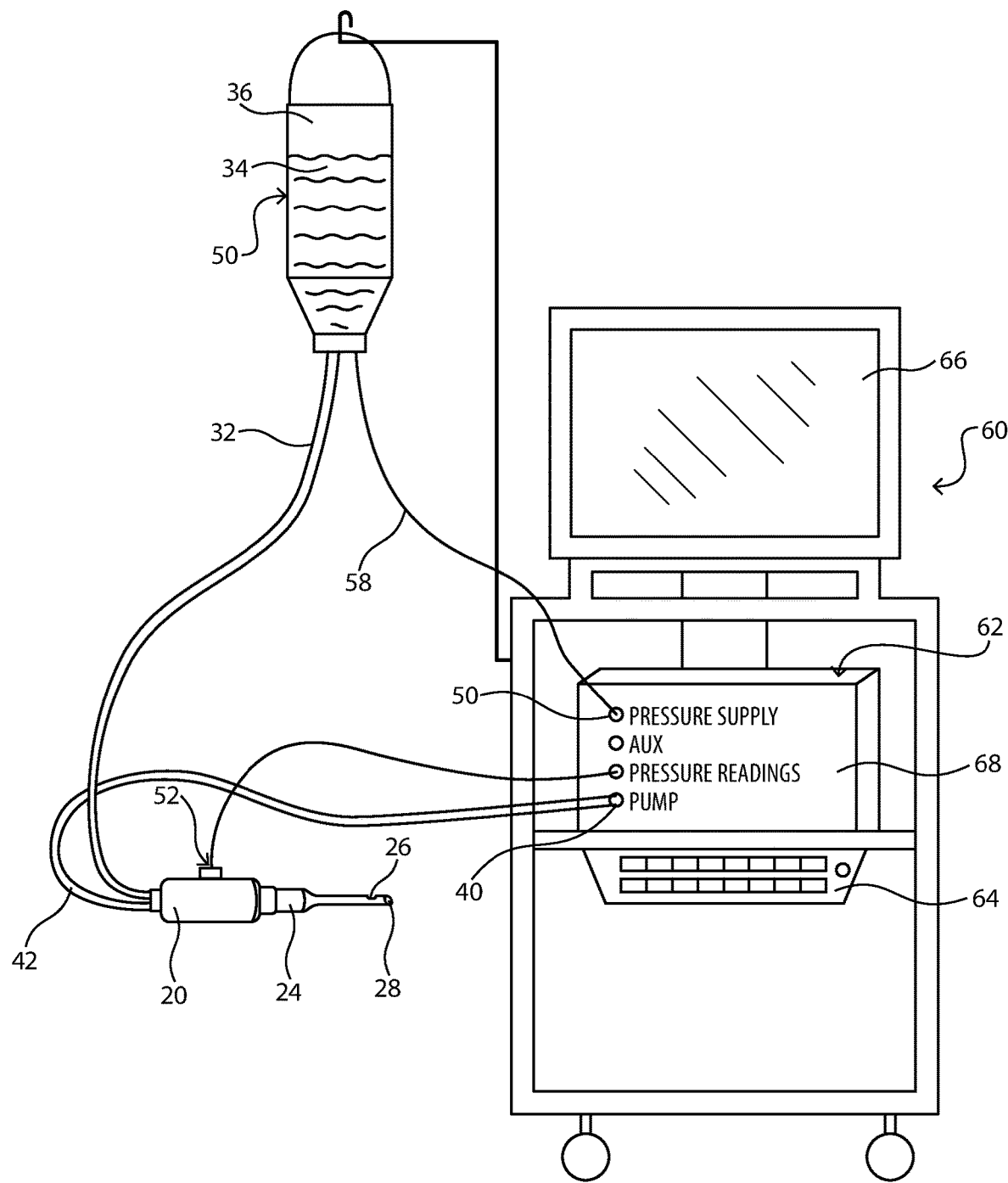
FIG. 6 is a perspective view of another embodiment of the system of the present disclosure.

As illustrated in FIGS. 4-6, illustrative embodiments of the present disclosure are directed to automatically detect the type of tip 24 attached to the handpiece 20 and adjust or set surgical criteria or system settings accordingly without surgeon or user input. Detection of tip characteristics may be made in a variety of surgical systems, including those using a vacuum-based system, a flow-based system, and/or the combination of both a vacuum-based and flow-based systems, for example. FIG. 4 illustrates a flow chart of a method 200 of detecting an attached tip 24 when using a vacuum-based system. In illustrative embodiments, the method may be implemented as a set of instructions on a computer readable medium within the control module 60. The beginning of the method 200 starts when a user or surgeon desires to use a uniform tip $X_1$ to a handheld device during a surgical operation such as a phacoemulsification operation. As illustrated in block 202, the user attaches the tip $X_1$ to the handheld device or handpiece 20. During a prime or tune cycle of the system 100, fluid is introduced into the system via the irrigation source 30 at a fluid flow rate of $R_1$, and a vacuum or constant pressure environment is created in the fluidic stream, as illustrated in block 204. Accordingly, the system is completely filled with fluid. At a point prior to the fluid flowing through the irrigation port 26, for example in the irrigation line 32, a sensor system 52 determines an input pressure $P_1$ of fluid flowing into the irrigation port 26, as illustrated in block 206.

At a point after fluid flows through tip $X_1$, as illustrated in block 208, the sensor system 52 determines an output pressure $P_2$, as illustrated in block 210. The input and output pressures $P_1$ and $P_2$ are sent to the control module 60 where they are analyzed by the control module 60 to identify the specific type of tip, $X_1$, being used on the handpiece 20, as illustrated in block 212. The control module 60 can then adjust various system settings, criteria or control characteristics of the system 100 in order to enhance or optimize the surgical procedure with tip $X_1$, as illustrated in block 214. At this point, the surgeon or user will use tip $X_1$ to perform various surgical action(s). Once finished, the surgeon may either choose remove the tip $X_1$ from the handheld device 20 if the surgical procedure is complete, as illustrated in block 216, or remove tip $X_1$ and attach a different tip, tip $X_2$, to the handheld device for additional surgical operations, as illustrated in block 218. If the surgeon attaches a new tip $X_2$ to the handheld device 20, another prime or tune cycle will be instituted in the system 100, and fluid can again be introduced into the system via the irrigation source 30 at a flow rate $R_2$ (which may be the same or different from $R_1$) to cause the system to be completely filed with fluid. Blocks 204-214 may then be repeated for operation with tip $X_2$ in order to enhance or optimize the surgical procedure with tip $X_2$. This process may be repeated as many times as necessary to calibrate or set the system 100 when and if a new or different tip is introduced to system 100.

Figure 7:
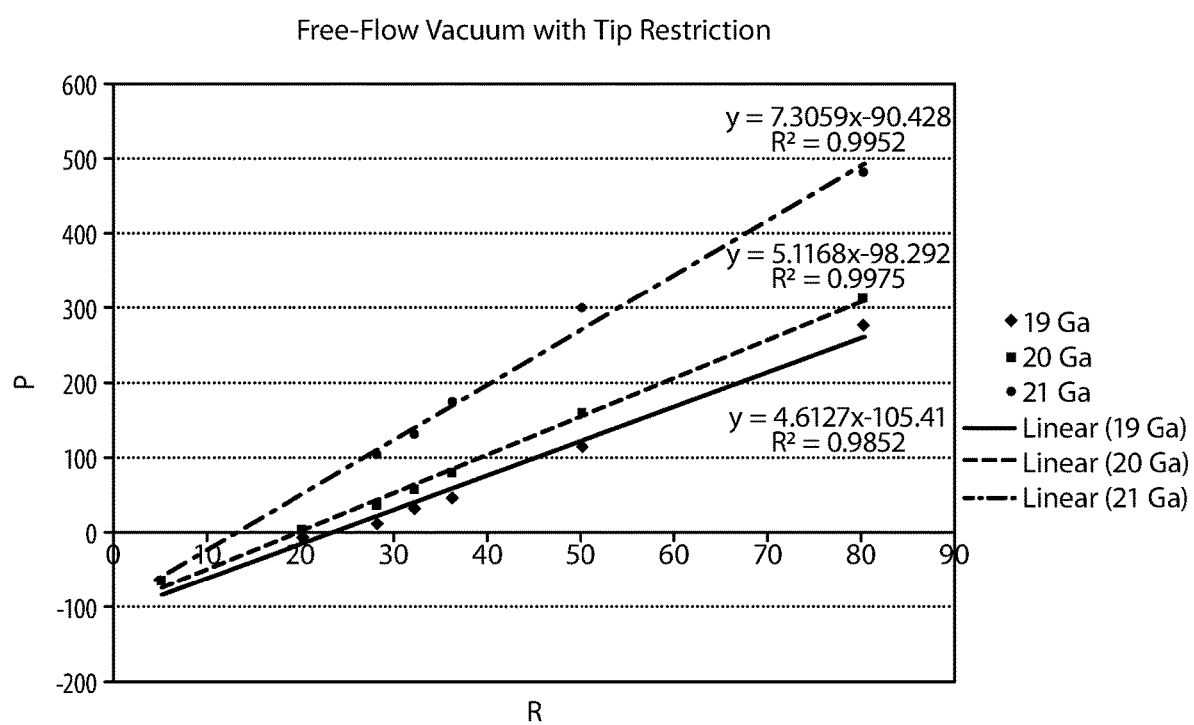
FIG. 7 is a graph showing known pressure and flow rate variable for various types of interchangeable multipurpose phacoemulsification tips.

FIG. 7 illustrates a graph of exemplar pressure measurements taken at various flow rates R for three standard or known tip 24 types (19Ga, 20 Ga, and 21 Ga). A similar type of exemplar measurement process may be performed for all standard or known tip types. Data for all standard or known tip 24 types may be stored in the control module 60 for future reference when automatic tip calibration is desired during a surgical operation. When the sensor system 52 (which may include one or more strain gauges) determines the input and/or output pressures P in the system 100 after a tip 24 is attached to the handpiece 20 and a specific flow rate R of fluid is flowing through the system, the input variables of the pressure P information and flow rate R information are analyzed in the control module 60 and compared to the data for known or standard tip types already determined, as illustrated in FIG. 7. Accordingly, the control module 60 may determine the specific tip 24 type based on the known pressure readings P at a predetermined flow rate R. As illustrated, it is envisioned that the difference between the types of tips 24 at one flow rate R is sufficient to determine which tip 24 is being used. Alternatively, two or more flow rates R may be used during the calibration of the tip 24, the input and output pressures P being determined at each flow rate, to provide two or more data points of comparison to determine the tip 24 type being used.

In illustrative embodiments, the sensor system 52 may be configured in a variety of ways or located in various locations. For example, the sensor system 52 may include at least a first sensor or strain gauge 54 and a second sensor or strain gauge 56, as illustrated in FIG. 1. At a point prior to the fluid flowing through the irrigation port 26, the first sensor 54, such as a vacuum sensor or pressure transducer, is utilized to detect a variety of variables, such as fluid pressure or vacuum level, of fluid flowing into the tip 24 of the handpiece 20. At a point after the fluid and materials flow through the aspiration port 28, the second sensor 56, which may also be a vacuum sensor or pressure transducer, may be utilized to detect similar variables of the fluid flowing out of the tip 24 of the handpiece 20. Other locations for the sensors 54 and 56 are envisioned anywhere along the irrigation line 32 and the aspiration line 42, respectively. In an embodiment, only one sensor may be used, for example on the aspiration line 42, the tip 24 or on the handpiece 20. In another embodiment, only one sensor may be used on the irrigation line 32. In another embodiment, multiple sensors may be used on the aspiration line, tip, and/or handpiece, and/or the irrigation line.

The irrigation source 30 is configured to deliver irrigation fluid in a steady, uniform flow rate R. In illustrative embodiments, the pressure supply 50 may be connected to the lower end of the irrigation source 30 such that pressurization of the irrigation source 30 is accomplished by a gas being delivered through pressure supply line 58, as illustrated in FIGS. 1 and 6. Thereafter, the gas may pass through any remaining irrigation fluid in the irrigation source 30 and into a pocket of gas 36 within the irrigation source 30 above the irrigation fluid. Such a connection to the lower end of the irrigation source 30 may be made through an IV spike, for example. In this way, the pressure supply line 58 may be suitable for use with any size irrigation source 30. In illustrative embodiments, both the pressure supply line 58 and the irrigation line 32 may be in fluidic communication with the irrigation source 30 through an IV spike. Further, an IV spike compatible for use with two lines may be constructed to withstand the increase in pressure provided by the system, and may include valves or backflow prevention mechanisms (not shown) to allow for reduction of pressure in, for example, the pressure supply line without the irrigation fluid entering the pressure supply line 58.

In an embodiment of the present invention, the pressurized gas 36 may be limited to a low pressure or low maximum available pressure, and may be constant so as to provide a stable and non-dynamic pressure to the irrigation source 30. In illustrative embodiments, the pressure supply 50 may include a pressurization device such as a compressor. As known in the art, the pressure supply 50 may be electronically controlled and monitored by the control module 60. The control module 60 may further measure and provide variables of the pressure supply 50 to a user or surgeon, and thereafter provide means for controlling the pressure supply 50.

In an alternative embodiment, instead of pressure supply 50, the amount of fluid supplied from irrigation source 30 may be controlled by gravity and an adjustable IV pole. The control module 60 may monitor the fluid flow from irrigation source 30 and adjust the IV pole to achieve a desired flow rate.

Similarly, the aspiration source 40 is configured to aspirate or remove fluid and other materials from the eye in a steady, uniform flow rate R. Various means for steady, uniform aspiration are well known in the art. In illustrative embodiments, the aspiration source 40 may be a venturi pump, a peristaltic pump, or a combined venturi and peristaltic pump. In illustrative embodiments, and as shown in FIG. 1, a peristaltic pump 44 may be configured to include a rotating pump head 46 having rollers 48. The aspiration line 42 is configured to engage with the rotating pump head 46 as it rotates about an axis. As the pump head 46 rotates the rollers 48 press against the aspiration line 42 causing fluid to flow within the aspiration line 42 in a direction of the movement for the rollers 48. Accordingly, the pump 44 directly controls the volume or rate of fluid flow, and the rate of fluid flow can be easily adjusted by adjusting the rotational speed of the pump head 46. Other means of uniformly controlling fluid flow in an aspiration source 40 are well-known in the art. When the aspiration source 40 includes a combined venturi and peristaltic pump, the aspiration source 40 may be controlled to automatically switch between the two types of pumps.

In illustrative embodiments, the control module 60 is configured to monitor and control various components of the system 100. For instance, the control module 60 may monitor, control, and provide power to the pressure supply 50, the aspiration source 40, and/or the handpiece 20. The control module 60 may be in a variety of forms as known in the art. In illustrative embodiments, the control module 60 may include a microprocessor computer 62, a keyboard 64 (which may be virtual displayed on a screen), and a display or screen 66, as illustrated in FIGS. 1 and 6. The microprocessor computer 62 may be operably connected to and control the various other elements of the system, while the keyboard 64 and display 66 permit a user to interact with and control the system components as well. In illustrative embodiments, the control module 60 may also include a pulsed ultrasonic power source (not shown) that can be controlled by the computer 62 in accordance with known methods or algorithms in the art. A system bus 68 may be further provided to enable the various elements to be operable in communication with each other.

The screen 66 may display various measurements, criteria or settings of the system 100—such as the type of procedure, the phase of the procedure F and duration of the phase D, flow rate R, the input and output pressures P, and the tip 24 the system has been calibrated for, as illustrated n FIG. 5. The screen 66 may be in the form of a graphical user interface (GUI) 70 associated with the control module 60 and utilizing a touchscreen interface, for example. The GUI 70 may allow a user to monitor the characteristics of the system 100 or select settings or criteria for various components of the system. For instance, the GUI 70 may permit a user to select or alter the maximum pressure being supplied by the pressure supply 50 to the irrigation source 30. The user may further control the operation of the phase of the procedure F, the units of measurement used by the system 100, the height of the irrigation source 30. In an embodiment of the present invention, the pressure reading P may be indicative of the total pressure of the irrigation line 32, and may combine measurements of both the irrigation source height and the pressure provided into the pressure supply line 58. In this way, for example, the GUI 70 may provide both an actual pressure reading based on direct measurement of the irrigation line 32, and a target or desired pressure based on the height of the irrigation source 30 and the pressure provided in the pressure supply line 58, if any. The GUI 70 may further allow for the calibration and priming of the pressure in the irrigation source 30. The GUI 70 may also provide other options for the user, such as, for example, allowing for cancelling priming and tuning by selecting a button 72.

The tip calibration process illustrated in FIG. 4 may be performed during the prime or tune phase of a surgical procedure. As illustrated in FIG. 5, the GUI 70 may display the status of the tip calibration process on the screen 66 for the user to monitor, and if necessary control. The GUI 70 may also provide other options for the user, such as, for example, allowing for cancelling of tip calibration by selecting a button 74. The GUI 70 can display the process of the tip calibration by showing, for example, the flow rate R, the input/out pressures P measured by the sensor system 52, and the resulting tip 24 determination based on comparison of the input variables (such as flow rate and input/output pressures P) to the known measurements of standard tips in the industry, as discussed above.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.), irrigation source height adjustment, linear control of settings, proportional control of settings, panel control of settings, and type (or "shape") of response.

The interface provides feedback to the user should the pre-selected or automatic settings or criteria need adjustment to ensure all the desired settings of the system. The interface can then permit the user to change or modify those settings accordingly.

Other mechanisms for setting and/or programming a particular setting may be employed with the present invention, including, but not limited to, clicking on an icon on a display screen using a mouse or touch screen, depressing a button/switch on a foot pedal, voice activated commands and/or combinations thereof.

The term "phacoemulsification" refers to a method of lens and cataract extraction from an eye. The procedure includes an ultrasonically vibrated needle which is inserted through a very small incision in the cornea in order to provide energy for emulsifying or breaking up of the lens and cataract which then can be aspirated and removed through the incision.

The term "vitrectomy surgery" refers to a method employed during cataract surgery when the posterior capsular bag has been broken and in the treatment of retinal detachments resulting from tears or holes in the retina. In cataract surgery, the same incision used for the phacoemulsification handpiece is used for inserting the vitrector to remove the vitreous gel. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion/aspiration port(s), but these devices may be combined into one single tool as well.

The term "screen," "display," or "display screen" as used herein shall mean a graphical user interface (GUI), a screen, a monitor, touch screen, or any other device known in the art for displaying a visual picture or representation.

The previous description is provided to enable any person skilled in the art to make or use the disclosed embodiments. Various modifications to these embodiments will be readily apparent to those skilled in the art, and the generic principles defined herein may be applied to other embodiments without departing from the spirit or scope of the invention. Thus, the present disclosure is not intended to be limited to the embodiments shown herein but is to be accorded the widest scope consistent with the principles and novel features disclosed herein.

The invention claimed is:

1. An ocular surgical apparatus comprising:
a handpiece configured to receive an interchangeable tip;
an irrigation line configured to transport fluid to the interchangeable tip, the irrigation line being connected to an irrigation source;
an aspiration line configured to transport fluid away from the interchangeable tip, the aspiration line connected to an aspiration source;
a sensor system configured to determine the pressure of fluid flowing in the aspiration line; and
a controller configured to determine a flow rate of fluid flowing through the apparatus, and further configured to receive information from the sensor system regarding the pressure of fluid flowing in the aspiration line; and
wherein the controller is further configured to compare the flow rate of the fluid flowing through the apparatus to known flow rate information of standard tips, and is configured to compare the pressure information received from the sensor system regarding the pressure of the fluid flowing in the aspiration line to known pressure information of standard tips, and further configured to determine the type of interchangeable tip attached to the handpiece based on the flow rate of the fluid flowing thorough the apparatus and the pressure information received from the sensor system regarding the pressure of the fluid flowing in the aspiration line, and
wherein the controller is configured to adjust one or more settings of the apparatus based on the type of interchangeable tip without user input.

2. The surgical apparatus of claim 1, wherein the interchangeable tip includes an irrigation port to receive fluid from the irrigation line.

3. The surgical apparatus of claim 2, wherein the interchangeable tip includes an aspiration port to remove fluid or materials via the aspiration line.

4. The surgical apparatus of claim 1, wherein the sensor system is further configured to determine the pressure of fluid flowing in the irrigation line.

5. The surgical apparatus of claim 4, wherein the controller is further configured to receive information from the sensor system regarding the pressure of fluid flowing in the irrigation line.

6. The surgical apparatus of claim 1, wherein the sensor system includes a first sensor along the aspiration line.

7. The surgical apparatus of claim 6, wherein the interchangeable tip includes an aspiration port to receive fluid from an eye through the aspiration line, and the first sensor is positioned adjacent the aspiration port.

8. The surgical apparatus of claim 7, wherein the first sensor determines the pressure of fluid flowing in the aspiration line and the flow rate of fluid flowing through the aspiration line.

9. The surgical apparatus of claim 7, wherein the sensor system includes a second sensor along the irrigation line.

10. The surgical apparatus of claim 9, wherein the interchangeable tip includes an irrigation port to receive fluid from the irrigation line, and the second sensor is positioned adjacent the irrigation port.

11. The surgical apparatus of claim 10, wherein the second sensor determines the pressure of fluid flowing in the irrigation line and the flow rate of fluid flowing through the irrigation line.

12. The surgical apparatus of claim 1, wherein the aspiration source is a venturi pump or a peristaltic pump.

13. The surgical apparatus of claim 1, wherein the aspiration source is a combination venturi pump and peristaltic pump.

14. The surgical apparatus of claim 1, further including a pressure supply that maintains a predetermined amount of pressure in the irrigation source.

15. A method of detecting an interchangeable tip of a handpiece of an ocular surgical system, the method comprising:
    attaching the interchangeable tip to the handpiece;
    introducing fluid flow into the system and determining a fluid flow rate of fluid flow in the system;
    determining the pressure of fluid flowing into the interchangeable tip;
    determining the pressure of fluid flowing out of the interchangeable tip to an aspiration source;
    comparing the determined fluid flow rate and the determined pressure information into and out of the interchangeable tip to known fluid flow rate and pressure readings of known types of interchangeable tips to determine the type of interchangeable tip being used;
    determining a set of surgical settings or system performance metrics for the system based on the interchangeable tip detected; and
    applying the surgical settings or metrics to the system automatically in order to have desired system performance during the surgical operation.

16. The method of claim 15, wherein the fluid flow is introduced into the system via an irrigation line connected to an irrigation source.

17. The method of claim 16, wherein the irrigation source is a drip bag.

18. The method of claim 17, wherein the method further comprises maintaining a predetermined amount of pressure in the irrigation source.

19. The method of claim 15, wherein the method further comprises using a venturi pump or a peristaltic pump to aspirate the fluid flowing out of the interchangeable tip.

20. The method of claim 19, wherein the fluid flowing out of the interchangeable tip carries ocular lens material.

21. The method of claim 15, wherein the method further comprises providing the set of surgical settings or system performance metrics to a user on a display.

22. The method of claim 21, wherein the method further comprises permitting a user to adjust or cancel the surgical settings or system performance metrics.

23. The method of claim 16, wherein the method further comprises providing a name or identification number of the interchangeable tip detected to a user on a display.

24. The method of claim 23, wherein the display permits the user to interactively modify or cancel applying the surgical settings or metrics to the system once the name or identification number of the interchangeable tip is provided.

* * * * *